(12) United States Patent
Lin et al.

(10) Patent No.: US 7,264,891 B2
(45) Date of Patent: Sep. 4, 2007

(54) ORGANIC ELECTROLUMINESCENT DEVICE AND ORGANIC ELECTROLUMINESCENT COMPOUND THEREOF

(75) Inventors: Hsien-Chang Lin, Jubei (TW); Chih-Hao Kung, Kaohsiung (TW); Chung-Cheng Pai, Taipei (TW); Shwu-Ju Shieh, Taipei (TW); Tzu-Chin Tang, Hsinchu (TW)

(73) Assignee: Rit Display Corporation, Hsinchu (TW)

( * ) Notice: Subject to any disclaimer, the term of this patent is extended or adjusted under 35 U.S.C. 154(b) by 110 days.

(21) Appl. No.: 10/695,655

(22) Filed: Oct. 27, 2003

(65) Prior Publication Data

US 2004/0131885 A1    Jul. 8, 2004

(30) Foreign Application Priority Data

Oct. 25, 2002    (TW) ............................... 91125124 A (51) Int. Cl.
*H01J 1/62* (2006.01)
(52) U.S. Cl. ...................... 428/690; 428/917; 313/504; 313/506; 252/301.16
(58) Field of Classification Search ........... 252/301.16; 313/504, 506; 428/690, 917; 548/217, 219, 548/235, 236, 304.4, 305.1, 305.7, 309.7, 548/152, 156, 202, 440; 564/305, 433, 434; 546/94, 98, 99; 540/588; 568/306, 327
See application file for complete search history.

(56) References Cited

U.S. PATENT DOCUMENTS 6,067,186 A * 5/2000 Dalton et al. ............... 359/321
6,348,992 B1 * 2/2002 Zhang et al. ................ 359/321
6,610,809 B1 * 8/2003 Yamamoto et al. ......... 526/292.2
6,616,865 B1 * 9/2003 Zhang et al. ................ 252/582
6,652,779 B1 * 11/2003 Zhang et al. ................ 252/582
6,653,421 B1 * 11/2003 Yamamoto et al. ......... 526/259

OTHER PUBLICATIONS

Jen et al., "Polyquinolines: Multifunctional polymers for electro-optic and light-emitting applications", Materials Research Society Symposium, vol. 558, (2000), pp. 469-480.*

* cited by examiner

*Primary Examiner*—Rena Dye
*Assistant Examiner*—Camie S. Thompson
(74) *Attorney, Agent, or Firm*—WPAT, P.C.; Anthony King

(57) ABSTRACT

An organic electroluminescent device comprises an anode disposed on a substrate, an organic electroluminescent layer disposed on the anode and a cathode disposed on the organic electroluminescent layer, wherein the organic electroluminescent layer comprises a compound represented by the formula (1) below

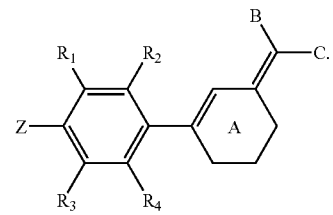

(1)

11 Claims, 2 Drawing Sheets

ORGANIC ELECTROLUMINESCENT DEVICE AND ORGANIC ELECTROLUMINESCENT COMPOUND THEREOF

CROSS-REFERENCE TO RELATED APPLICATION

This application claims the priority benefit of Taiwan application serial no. 91125124, filed on Oct. 25, 2002.

BACKGROUND OF THE INVENTION

1. Field of the Invention

The present invention relates to an organic electroluminescent device, and more particularly to a red-light organic electroluminescent device and an organic electroluminescent compound applied thereto.

2. Description of the Related Art

Because of low weight and high efficiency, flat panel displays, such as liquid crystal displays, have been widely developed. However, liquid crystal displays have some problems, such as viewing angle, response speed, driving power and color. More particularly, liquid crystal displays cannot be fabricated with large size.

To date, organic electroluminescent displays have gradually overcome the size issue and above-mentioned problems The organic electroluminescent devices perform display by using organic electroluminescent material. The device includes two electrodes and an organic electroluminescent layer between the electrodes. When a current or voltage is applied to the device, holes from the anode will recombine with electrons form the cathode within the organic electroluminescent layer and generate excitons. When the excitons release energy and are back to the ground state, a portion of energy generated therefrom will transfer into photons.

In Applied Physics Letters, Vol. 51, No. 12, pp 913-915 (1987), C. W. Tang and S. A. VanSlyke disclosed a double-layer organic electroluminescent device, which includes a pair of electrodes, an organic electroluminescent layer and a hole or electron transporting layer. When electrons and holes are injected by the electrodes and go through the electron or hole transporting layer, they recombine within the organic electroluminescent layer and generate photons. The colors of light generated from the device depend on the electroluminescent material.

In Japanese Journal of Applied Physics, Vol. 27, No. 2, pp L269-L271(1988) and Journal of Applied Physics, Vol65, No. 9, pp. 3610-3616 (1989), a triple-layer organic electroluminescent device is disclosed, which includes a pair of electrodes, an organic electroluminescent layer, a hole transporting layer and an electron transporting layer. Moreover, it also showed that low driving voltage and high brightness are feasible.

For full-color display, purity of colors is very essential. The advantage of organic electroluminescent material is that the wavelengths of the lights can be tuned by modifying the structure of the compounds thereof.

However, some issues of the organic electroluminescent device should be overcome, especially in stability and efficiency of the organic electroluminescent device. Traditionally, tris(8-quinolinol) aluminum (AlQ3) doped with DCM or its derivatives are used as the red-light organic electroluminescent layer. The material still cannot provide organic electroluminescent device with high brightness and good color purity.

SUMMARY OF THE INVENTION

Therefore, the present invention is to provide an organic electroluminescent device and an organic electroluminescent compound thereof for full-color displays.

The present invention is also to provide an organic electroluminescent device and an organic electroluminescent compound thereof utilized for an organic electroluminescent device having high stability, high efficiency and good color purity.

The present invention discloses an organic electroluminescent device, which comprises a transparent substrate; an anode disposed on the transparent substrate; an organic electroluminescent layer disposed on the anode; and a cathode disposed on the organic electroluminescent layer, wherein the organic electroluminescent layer comprises a compound represented by a formula (1) below:

(1)

wherein $R_1 \sim R_4$ are comprised of hydrogen, substituted or unsubstituted alkyl group, substituted or unsubstituted cycloalkyl group, substituted or unsubstituted alkyloxy group, substituted or unsubstituted alkenyl group, substituted or unsubstituted amino group, substituted or unsubstituted polycyclic aromatic group or a combination thereof; Z is a electron-donating groups, such as $-NR_5R_6$; A is substituted or unsubstituted cyclohexene or naphthalene group as shown in formula (2); and B and C are electron withdrawing groups, which can be same or different substitutes, such as cyano, indandione, benzoimidazole, benzooxazole, or benzothiazole group.

In detail, $R_1 \sim R_4$ can be a hydrogen, substituted or unsubstituted alkyl group having 1 to 10 carbons, substituted or unsubstituted cycloalkyl group having 1 to 10 carbons, substituted or unsubstituted alkyloxy group having 1 to 10 carbons, substituted or unsubstituted alkenyl group having 1 to 10 carbons, substituted or unsubstituted amino group, substituted or unsubstituted polycyclic aromatic having 6 to 10 carbons. $R_5$ and $R_6$ can be a hydrogen, substituted or unsubstituted alkyl group having 1 to 10 carbons, substituted or unsubstituted cycloalkyl group having 1 to 10 carbons, substituted or unsubstituted alkyloxy group having 1 to 10 carbons, substituted or unsubstituted alkenyl group having 1 to 10 carbons, substituted or unsubstituted amino group, substituted or unsubstituted polycyclic aromatic group having 6 to 10 carbons.

(2)

In formula (2), $R_8$~$R_{16}$ are a hydrogen, substituted or unsubstituted alkyl group, substituted or unsubstituted cycloalkyl group, substituted or unsubstituted alkyloxy group, substituted or unsubstituted alkenyl group, substituted or unsubstituted amino group, substituted or unsubstituted polycyclic aromatic group or a combination thereof. B and C are electron withdrawing groups, which can be same or different substitutes, such as cyano, indandione, benzoimidazole, benzooxazole or benzothiazole as shown in formulas (3)-(5).

The organic electroluminescent layer of the organic electroluminescent device of the present invention enhances the thermal stability of the process by using cycloalkene skeleton. Therefore, a red-light organic electroluminescent device having high stability, high efficiency and good color purity is provided. Moreover, the red-light organic electroluminescent compound is suitably used in full-color organic electroluminescent displays.

In order to make the aforementioned and other objects, features and advantages of the present invention understandable, a preferred embodiment accompanied with figures is described in detail below.

DESCRIPTION OF SOME EMBODIMENTS

Figure 1:
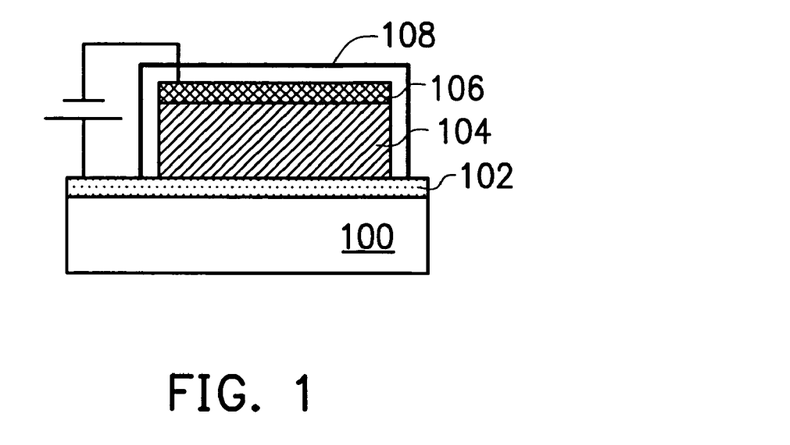
FIG. 1 is a schematic cross-sectional view of an exemplary organic electroluminescent device of the present invention.

FIG. 1 is a schematic cross-sectional view of an exemplary organic electroluminescent device of the present invention.

Referring to FIG. 1, the organic electroluminescent device is a single-layer structure, which comprises a transparent substrate 100, an anode 102, an organic electroluminescent layer 104, a cathode 106 and a protective layer 108.

The transparent substrate 100 is, for example, a glass substrate, a plastic substrate or a flexible substrate.

The anode 102 is disposed on the transparent substrate 100, utilized for injecting holes into the organic electroluminescent layer 104. Therefore, a preferred work function of the anode 102 is above 4.5 eV. The anode can be indium tin oxide (ITO), tin oxide, gold, silver, Pt or copper.

The organic electroluminescent layer 104 is disposed on the anode 102, which has the property of electroluminescence and transports electrons and holes. In the present invention, the detail descriptions of the organic electroluminescent layer 104 will be described below.

The cathode 106 is disposed on the organic electroluminescent layer 104, utilized for injecting electrons into the organic electroluminescent layer 104. It is preferred that the cathode 106 has a smaller work function. The cathode 106 can be, for example, In, Al, MgIn, MgAl, AlLi or MgAg.

The protective layer 108 completely covers the organic electroluminescent device and prevents the organic electroluminescent device from erosion by moisture and oxygen.

The current applied to the organic electroluminescent device can be direct current, alternative current or plus current. In addition, the electroluminescence of the organic electroluminescent device can pass through the anode 102 or reflect from the cathode 106.

Figure 2:
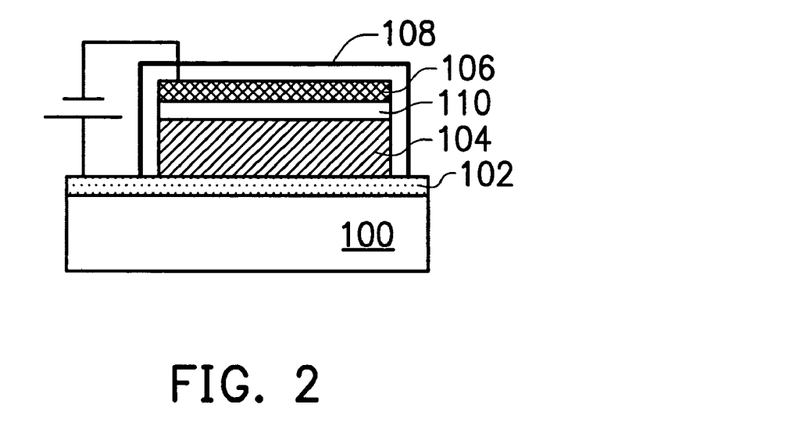
FIGS. 2 and 3 are schematic cross-sectional views of double-layer organic electroluminescent device of the present invention.
Figure 3:
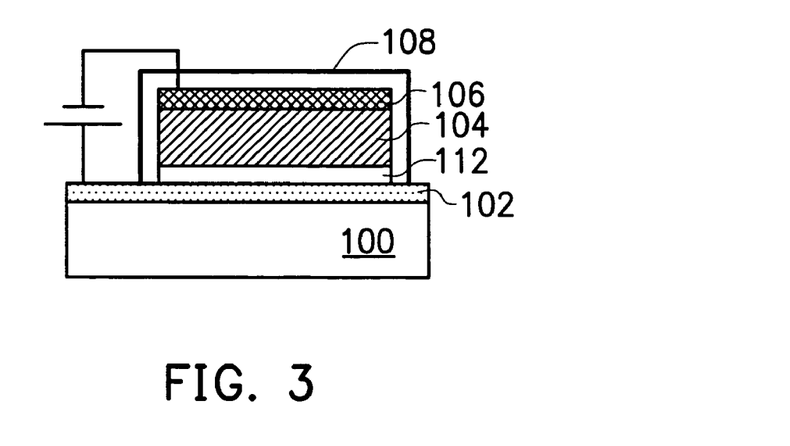

The organic electroluminescent device of the present invention can also be a double-layer structure as show in FIGS. 2 and 3. Please referring to FIG. 2, the double-layer structure further comprises an electron transporting layer 110 between the organic electroluminescent layer 104 and the cathode 106. Referring to FIG. 3, the double-layer structure further comprises a hole transporting layer 112 between the organic electroluminescent layer 104 and the anode 102.

Figure 4:
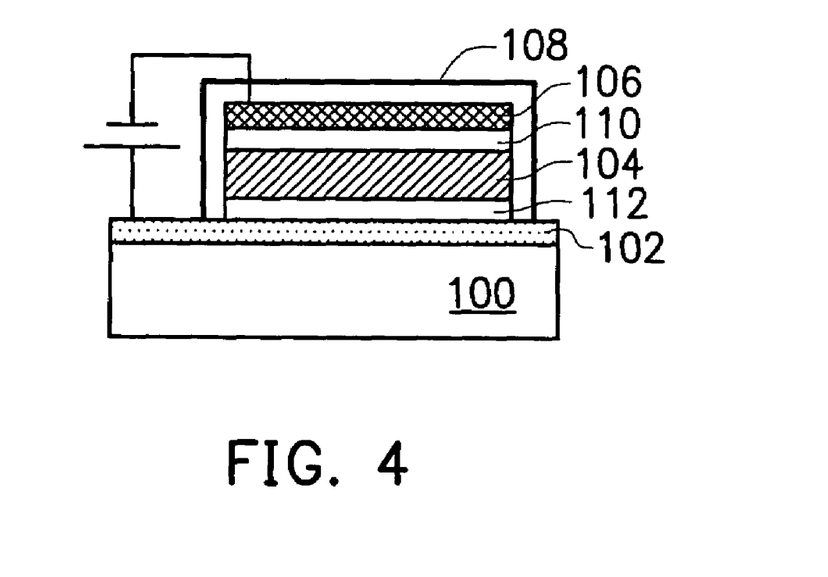
FIG. 4 is a schematic cross-sectional view of a triple-layer organic electroluminescent device of the present invention.

Moreover, the organic electroluminescent device of the present invention can also be a triple-layer structure as show in FIG. 4. Please referring to FIG. 4, the triple-layer structure further comprises an electron transporting layer 110 between the organic electroluminescent layer 104 and the cathode 106, and a hole transporting layer 112 between the organic electroluminescent layer 104 and the anode 102.

Figure 5:
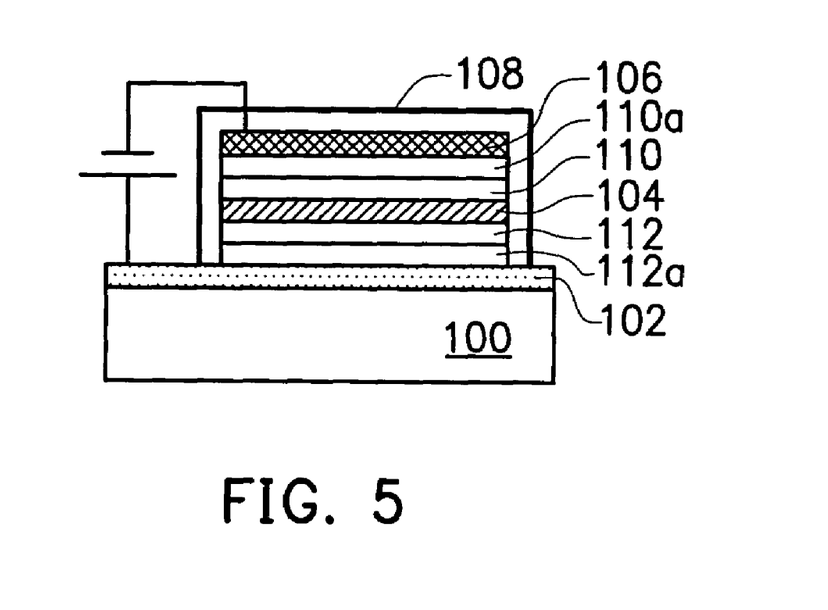
FIG. 5 is a schematic cross-sectional view of a five-layer organic electroluminescent device of the present invention.

Additionally, the organic electroluminescent device of the present invention can also be a five-layer structure as show in FIG. 5. Referring to FIG. 5, the five-layer structure further comprises an electron injection layer 110a between the electron transporting layer 110 and the cathode 106, and a hole injection layer 112a between the hole transporting layer 112 and the anode 102.

In the organic electroluminescent device described above, the organic electroluminescent layer 104 is the feature of the present invention, which is an organic electroluminescent material applied to red-light organic electroluminescent device. The detail descriptions are as shown below.

The organic electroluminescent device of the present invention comprises a compound represented by formula (1) below.

(1)

wherein $R_1$~$R_4$ are comprised of hydrogen, substituted or unsubstituted alkyl, substituted or unsubstituted cycloalkyl group, substituted or unsubstituted alkyloxy group, substituted or unsubstituted alkenyl, substituted or unsubstituted amino, substituted or unsubstituted polycyclic aromatic group or a combination thereof; Z is a electron donating groups, such as —$NR_5R_6$; A is substituted or unsubstituted cyclohexene or naphthalene group as shown in formula (2); and B and C are electron withdrawing groups, which can be same or different substitutes, such as, cyano, indandione, benzoimidazole, benzooxazole or benzothiazole.

The $R_1$~$R_4$ can be a hydrogen, substituted or unsubstituted alkyl having 1 to 10 carbons, substituted or unsubstituted cycloalkyl having 1 to 10 carbons, substituted or unsubstituted alkyloxy having 1 to 10 carbons, substituted or unsubstituted alkenyl having 1 to 10 carbons, substituted or unsubstituted amino or substituted or unsubstituted polycyclic aromatic having 6 to 10 carbons. $R_5$ and $R_6$ can be a hydrogen, substituted or unsubstituted alky having 1 to 10 carbons, substituted or unsubstituted cycloalkyl having 1 to 10 carbons, substituted or unsubstituted alkyloxy having 1 to 10 carbons, substituted or unsubstituted alkenyl having 1 to 10 carbons, substituted or unsubstituted amino or substituted or unsubstituted polycyclic aromatic having 6 to 10 carbons.

(2)

In formula (2), $R_8$~$R_{16}$ are a hydrogen, substituted or unsubstituted alky, substituted or unsubstituted cycloalkyl, substituted or unsubstituted alkyloxy, substituted or unsubstituted alkenyl, substituted or unsubstituted amino, substituted or unsubstituted polycyclic aromatic or a combination thereof. B and C are electron withdrawing groups, which can be same or different substitutes, such as cyano, indandione, benzoimidazole, benzooxazole or benzothiazole as shown in formulas (3)-(5).

(3)

(4)

(5)

Following are embodiments of the compounds within the organic electroluminescent device of the present invention, which are a portion of the formula (1), but not limited thereto.

(3-1)

(3-2)

(3-3)

(3-4)

(3-5)

(3-6)

(3-7)

(3-8)

(3-9)

(3-10)

(4-1)

-continued

(4-2)

(4-3)

(4-4)

(4-5)

-continued

(4-6)

(4-7)

(4-8)

(4-9)

-continued

(5-1)

(5-6)

(5-2)

(5-7)

(5-3)

(5-8)

(5-4)

(5-9)

(5-5)

(5-10)

-continued (5-11)

(5-12)

(5-13)

(5-14)

(5-15)

-continued (5-16)

(5-17)

(5-18)

(5-19)

(5-20)

-continued (5-21)

(5-22)

(5-23)

(5-24)

(5-25)

-continued

(5-26)

(5-27)

(5-28)

(5-29)

(5-30)

(5-31)
(5-32)
(5-33)
(5-34)
(5-35)
(5-36)

(5-37)
(5-38)

Additionally, the mixture of the compound represented by formula (1) and metal complex, such as AlQ3, can provide high performance of red-light organic electroluminescent device.

In the organic electroluminescent device of the present invention, the organic electroluminescent layer can be formed by a deposition process, such as vacuum evaporation, molecular beam epitaxy (MBE), immersion in a solution, spin coating, casting, bar code, roll coating, etc. The thickness of the organic electroluminescent layer is not specified. If the layer is too thin, pinholes will occur; if it is too thick, a higher voltage should be applied. Therefore, it is preferred that the thickness of the organic electroluminescent layer is from about 1 nm to about 1 μm.

Additionally, the material of the hole transporting layer is not specified. Any material adapted to serve as the hole transporting layer can be used, such as TPD or NPB(α-naphylhenyldiamine) as shown below.

TPD

-continued

NPB

Additionally, the material of the electron transporting layer is not specified. Any material adapted to serve as the electron transporting layer can be used, such as AlQ3, Bebq2, TAZ or PBD as shown below.

AlQ3

Bebq2

TAZ

PBD

In the organic electroluminescent device of the present invention, the methods of forming the electron transporting layer, the hole transporting layer, the electron injection layer and the hole injection layer are not specified. Any traditional deposition method, such as vacuum evaporation or spin coating, can be used. Additionally, the thickness of the electron transporting layer, the hole transporting layer, the electron injection layer and the hole injection layer are not specified. Generally, if the films are too thick, a high voltage is required to be applied thereto. Therefore, preferably the thickness of the electron transporting layer, the hole transporting layer, the electron injection layer and the hole injection layer can be from about 1 nm to about 1 μm.

Following are two examples to synthesize the organic electroluminescent compound and two organic electroluminescent devices thereof. But the scope of the invention is not limited thereto.

Following is the first example to synthesize the compound represented by formula (3-5).

1.5 g (4.6 mmole) (4-bromo-phenyl)-diphenyl-amine was dissolved in 20 ml dry THF under nitrogen. 3.2 ml 1.6 M n-BuLi (4.6 mmole×1.1) was added into the solution at −78° C., and the reaction mixture was then stirred at −78° C. for three hours. Then 0.94 g (4.6 mmole) 7-methoxy-5,5-dimethyl-2,3,4,4a,5,6-hexahydro-naphthalenone dissolved in 10 ml dry THF was added into mixture solution at −78° C. The solution was stirred overnight. Water and 30 ml ethyl acetate and acetic acid are added into solution. Then, the aqueous layer was the separated and extracted with ethyl acetate(3× 30 ml). The combined organic layers dry over MgSO4, filtered and solvent removed by rotary evaporation. Purification by column chromatography over silica to obtain the compound (0.63 g) represented by the following chemical structure (3-5-a). The yield is 33%.

(3-5-a)

7-(4-Diphenylamino-phenyl)-4,4-dimethyl-
4,4a,5,6-tetrahydro-3H-naphthalen-2-one

Then, 0.5 g (1.2 mmole) of the above compound shown in (3-5-a), 0.1 ml piperidine and 0.23 g (1.2 mmole×3) malononitrile was dissolved in 20 ml acetonitrile. The solution was then refluxed for 24 hours. Purified water and dichloromethane was then added into the solution, then, the aqueous layer was separated and extracted with t dichloromethane (30 mlX3). The combined organic layers dry over MgSO4, filtered and solvent removed by rotary evaporation. Purification by column chromatography over silica obtain 0.196 g of compound represented by following chemical structure (3-5) is obtained. The yield is 35%.

(3-5)

Following is the second example to synthesize the compound represented by formula (3-3).

First, 2 g (8 mmole) 9-bromo-2,3,6,7-tetrohydro-1H,5H-pyrido[3,2,1-ij] quinoline was dissolved in 20 ml THF under nitrogen. 35.5 ml (8 mmole×1.1) 1.6 M n-BuLi (4.6 mmole×1.1) is added into the solution at −78° C. and stirred for three hoursi. Then 1.64 g (8 mmole) 7-methoxy-5,5-dimethyl-2,3,4,4a,5,6-hexahydro-naphthalenone dissolved in 10 ml THF was added into the solution at −78° C. and the mixture solution was stirred overnight. Purified water, 30 ml ethyl acetate and acetic acid are added into the mixture solution. Then, the aqueous layer was separated and extracted with ethyl acetate (30 mlX3). The combined organic layers dry over MgSO4, filtered and solvent removed by rotary evaporation. Purification by column chromatography over silica obtain the compound (1.1 g) represented by the following chemical structure (3-3-a). The yield is 40%.

(3-3-a)

4,4-Dimethyl-7-(2,3,6,7-tetrahydro-1H,5H-pyrido
[3,2,1-ij]quinolin-9-yl)-4,4a,5,6-tetrahydro-3
H-naphthalen-2-one Then, 0.5 g (1.44 mmole) of the compound shown in (3-3-a), 0.28 g (1.44 mmole×3) malononitrile and 0.1 ml piperidine was dissolved in 20 ml acetonitrile. The solution was then refluxed for 24 hours. Purified water and CH2Cl2 was then added into the solution. Then, the aqueous layer was separated and extracted with CH2Cl2(30 mlX3). The combined organic layers dry over MgSO4, filtered and solvent removed by rotaryevaporation. Purification by column chromatography over silica obtain 0.21 g compound represented by the following chemical structure (3-5) is obtained. The yield is 37%.

(3-3)

Following is a method of forming a triple-layer structure of the organic electroluminescent device. Referring to FIG. 4, a 100 mm×100 mm thick glass substrate 100 is provided. An ITO having a thickness of about 150 nm is formed on the substrate 100. An anode 102 is formed by forming a number of patterned ITO having size 10 mm×10 mm by photolithography and etch processes. Then a hole transporting layer 112 having thickness about 70 nm is formed on the anode 102 by a vacuum evaporation under 10-5 Pa, wherein the hole transporting layer 112 is NPB and the deposition rate is about 0.2 nm/sec.

Then, compound of formula (1) and AlQ3 are formed on the hole transporting layer with a deposition rate of about 0.2 nm/sec and 0.004 nm/sec respectively for forming the organic electroluminescent layer 104 with a thickness of about 20 nm.

An electron transporting layer 110, AlQ3, is formed on the organic electroluminescent layer 104, wherein the electron transporting layer 110 has a thickness about 25 nm and is formed at a deposition rate of about 0.2 nm/sec.

A LiF layer having thickness about 1.2 nm and an Al layer having thickness about 150 nm are formed on the electron transporting layer 110, utilized as a cathode 106. Thus, the fabrication of the organic electroluminescent device is completed.

The measurement of the organic electroluminescent device of the present invention is performed by using Keithly 2000. According to the results, the organic electroluminescent device emits red light, the maximum brightness is 1915 cd/m$^2$, CIE (0.58, 0.36), and the initial driving voltage is 3V.

According to the method of forming the organic electroluminescent device of the present invention, the compound of formula (1) is substituted by another compound and another device is formed therefrom.

According to the results, the organic electroluminescent device emits red light, the maximum brightness is 1128 cd/m$^2$, CIE (0.59, 0.31), and the initial driving voltage is 3.5V.

The organic electroluminescent layer of the organic electroluminescent device of the present invention enhances the thermal stability of the process by using cycloalkene skeleton. Therefore, a red-light organic electroluminescent device having high stability, high efficiency and good color purity is provided. Moreover, the red-light organic electroluminescent compound is suitably used in full-color organic electroluminescent displays.

Although the present invention has been described in terms of exemplary embodiments, it is not limited thereto. Rather, the appended claims should be constructed broadly to include other variants and embodiments of the invention which may be made by those skilled in the field of this art without departing from the scope and range of equivalents of the invention.

What is claimed is:

1. An organic electroluminescent device, comprising:
    a transparent substrate;
    an anode, disposed on the transparent substrate;
    an organic electroluminescent layer, disposed on the anode; and
    a cathode, disposed on the organic electroluminescent layer, wherein a material of the organic electroluminescent layer is a compound represented by a following chemical structure (1):

(1)

wherein R$_1$~R$_4$ are hydrogen, substituted or unsubstituted alkyl group, substituted or unsubstituted cycloalkyl group, substituted or unsubstituted alkyloxy group, substituted or unsubstituted alkenyl group, substituted or unsubstituted amino group, substituted or unsubstituted polycyclic aromatic group or a combination thereof; Z is a electron-donating group and is —$NR_5R_6$, wherein $R_5$ and $R_6$ are respectively a hydrogen, substituted alkyl having 1 to 10 carbons, unsubstituted alkyl having 1 to 10 carbons, substituted cycloalkyl having 1 to 10 carbons, unsubstituted cycloalkyl having 1 to 10 carbons, substituted alkyloxy having 1 to 10 carbons, unsubstituted alkyloxy having 1 to 10 carbons, substituted alkenyl having 1 to 10 carbons, unsubstituted alkenyl having 1 to 10 carbons, substituted amino, unsubstituted amino, substituted polycyclic aromatic having 6 to 10 carbons or unsubstituted polycyclic aromatic having 6 to 10 carbons; A is substituted or unsubstituted cyclohexene or naphthalene group; and B and C are electron withdrawing groups and attached to A as separate groups.

2. The organic electroluminescent device of claim 1, wherein B and C can be same or different substitutes.

3. The organic electroluminescent device of claim 1, wherein B and C are selected from the group consisting of cyano, benzoimidazole, benzooxazole and benzothiazole substitutes, or B and C are merged together as indandione substitutes.

4. The organic electroluminescent device of claim 1, wherein the material of the organic electroluminescent layer further comprises an aromatic amino compound, an aromatic diamond compound or an aromatic triamine compound having poly-cyclic ring aromatic substitutes or aromatic hydroxyl substitutes.

5. The organic electroluminescent device of claim 1, wherein the material of the organic electroluminescent layer further comprises a metal complex.

6. The organic electroluminescent device of claim 5, wherein the metal complex comprises AlQ3.

7. The organic electroluminescent device of claim 1, further comprising an electron transporting layer disposed between the cathode and the organic electroluminescent layer.

8. The organic electroluminescent device of claim 7, further comprising an electron injection layer is disposed between the cathode and the electron transporting layer.

9. The organic electroluminescent device of claim 1, further comprising a hole transporting layer disposed between the anode and the organic electroluminescent layer.

10. The organic electroluminescent device of claim 9, further comprising a hole injection layer is disposed between the anode and the hole transporting layer.

11. The organic electroluminescent device of claim 1, wherein the organic electroluminescent layer has a thickness from about 1 nm to about 1 μm.

* * * * *